United States Patent
Wada

[11] Patent Number: 6,129,718
[45] Date of Patent: Oct. 10, 2000

[54] URINE-RECEIVING PAD FOR MEN

[75] Inventor: Ichiro Wada, Kagawa, Japan

[73] Assignee: Uni-Charm Corporation, Ehime, Japan

[21] Appl. No.: 09/150,796

[22] Filed: Sep. 10, 1998

[30] Foreign Application Priority Data

Sep. 17, 1997 [JP] Japan ................................. 9-251764

[51] Int. Cl.⁷ ................................................. A61F 13/15
[52] U.S. Cl. .................... 604/378; 604/369; 604/370; 604/372; 604/374; 604/380; 604/383; 604/385.01; 604/385.01 M; 604/385.03; 604/385.24
[58] Field of Search .................................. 664/369, 378, 664/380, 383, 385.1, 388.2, 386, 387, 392–402, 374, 346–353, 370, 372, 385.01, 388.03, 385.24; 602/67–73

[56] References Cited

U.S. PATENT DOCUMENTS

| | | | |
|---|---|---|---|
| 3,403,410 | 10/1968 | Benzel et al. ......................... | 604/380 |
| 4,820,290 | 4/1989 | Yahr ..................................... | 604/349 |
| 4,863,448 | 9/1989 | Berg ..................................... | 604/349 |
| 4,886,509 | 12/1989 | Mattsson . | |
| 4,963,137 | 10/1990 | Heyden . | |
| 5,084,037 | 1/1992 | Barnett ................................. | 604/349 |
| 5,342,332 | 8/1994 | Wheeler . | |
| 5,745,926 | 5/1998 | Cailleteau ............................ | 604/350 |
| 5,827,250 | 10/1998 | Fujioka et al. ..................... | 604/385.2 |

FOREIGN PATENT DOCUMENTS

| | | | |
|---|---|---|---|
| 0998904 | 10/1976 | Canada ................................. | 604/350 |
| 0 123 661 | 10/1984 | European Pat. Off. .............. | 604/349 |
| 0228353 | 7/1987 | European Pat. Off. . | |
| 2701389 | 8/1994 | France . | |
| 63-160815 | 10/1988 | Japan . | |
| 4-44913 | 4/1992 | Japan . | |
| 6-26828 | 4/1994 | Japan . | |
| 81/03609 | 12/1981 | WIPO . | |
| 8402070 | 6/1984 | WIPO ................................... | 604/349 |
| 8911839 | 12/1989 | WIPO ................................... | 604/349 |

*Primary Examiner*—John G. Weiss
*Assistant Examiner*—K. M. Reichle
*Attorney, Agent, or Firm*—Koda & Androlia

[57] ABSTRACT

A urine-receiving pad for men including a bag of a laminated sheet which includes an inner sheet, an outer sheet and an absorbent core therebetween, and a pair of elastic members provided along the opening. By holding and pushing both ends of the elastic members with fingers, the elastic members are buckling-deformed to open the opening. When a penis is inserted into the opening and then the fingers are released, the penis is suitably pressed by elastic restoration forces of the elastic members, to prevent easy coming out of the penis therefrom. Since the pressing force resulting from the buckling-deformation of the elastic members is so small, too much pressure onto the penis is prevented. Further, the urine-receiving pad can be attached with only one hand.

7 Claims, 4 Drawing Sheets

URINE-RECEIVING PAD FOR MEN

BACKGROUND OF THE INVENTION

1. Field of the Invention

The present invention relates to a urine-receiving pad for men, to be applied to sick person, old people and incontinent patients, in which a laminated sheet having an absorbent core is formed into a bag into which a penis can be inserted.

2. Prior Art

A conventional urine-receiving pad for sick person, old people and incontinent patients is a sheet-shaped urine-receiving pad having an absorbent core to envelop a penis. A diaper is then applied to a wearer to secure the urine-receiving pad in position. However, since this sheet-shaped urine-receiving pad should be deformed into a shape for enveloping the penis, it is difficult to wear. Further, there is a problem of easy leakage of urine from the top of the pad thus deformed.

Accordingly, Japanese Laid-Open Utility Model Publication Nos. 160815/1988, 44913/1992 and 26828/1994 disclose urine-receiving pads provided with an opening for insertion of a penis.

However, this type of prior urine-receiving pad suffers from the problem that when a wearer moves or turns over, the penis easily comes out of the opening for insertion, or when much urine is excreted, urine leaks through the opening for insertion to the outside of the pad.

This is because there are differences in shape, size and direction of the penis in individuals. Therefore, it is difficult to form the opening for insertion fitting for all penises. Further, even if the opening for insertion fits for the penis at the time of wearing the pad, the penis may be excessively compressed by the opening by swelling of the penis.

Accordingly, it is necessary for the opening to be broad enough to receive the penis, which however results in easy coming out of the penis from the opening and easy leakage of urine through a gap formed between the opening and the penis.

Further, because the shape of the opening for insertion is unstable, a person who looks after a wearer is required to hold the penis of the wearer directly with one hand while spreading the opening widely with the other hand, to insert the penis therein.

The present invention is to solve the above-described problems in the prior art, and an object of the present invention is to provide a urine-receiving pad for men which can be easily attached to a penis and removed therefrom, while preventing easy coming out of the penis during use.

Another object of the present invention is to provide a urine-receiving pad for men which is wearable without touching the penis directly with hand.

Another object of the present invention is to provide a urine-receiving pad for men where urine hardly leaks from the opening for insertion of the penis.

SUMMARY OF THE INVENTION

The present invention provides a urine-receiving pad for men comprising a bag having an opening, which is formed from at least one laminated sheet having a liquid-permeable inner sheet, a liquid-impermeable outer sheet and an absorbent core provided between both the sheets. The bag is applied to a penis in such a manner that the penis is inserted into the opening, and a pair of plate-shaped or linear elastic members being disposed along an edge of the opening for sandwiching the penis by elastic restoration forces of the elastic members in a state of buckling-deformation.

In the urine-receiving pad of the present invention, the opening is opened by pushing the elastic members from both ends in the extending direction thereof with fingers, causing buckling-deformation. When the penis is inserted into the opening thus opened and then the fingers are released from both the ends, the buckling-deformed elastic members press the penis from both sides, by elastic restoration forces each trying to restore the original flat state before buckling-deformation. Accordingly, the penis is prevented from easily coming out of the opening thereafter.

The elastic member is may be made of plastic, into a plate, a rod or the like, but in consideration of incineration after disposal, the elastic member is preferably made of paper, cardboard, or the cardboard impregnated with reinforcing resin, into a plate, a rod or the like shape.

Further, foamed resin such as foamed polyurethane and foamed polyethylene is also preferable as a material to make the elastic member, because of its lightness and excellency in feelings during use.

In the present invention, preferably, the laminated sheet is folded in two toward the inner sheet in a laminating direction of the laminated sheet, and a folded side of the laminated sheet forms a bottom of the bag, and the laminated sheet is sealed along sides extending from the folded side, to form the bag having the opening.

Because the bottom of the bag is the folded side of the laminated sheet, urine is prevented from leaking from the bottom.

Further, it is preferable that the laminated sheet is extended from a part of the edge of the opening in a direction opposite to the bottom of the bag to form a leakage absorption portion.

When the penis is inserted into the bag, this leakage absorption portion is applied to the testes and further to a crotch of a wearer. Accordingly, even if urine is leaked from the opening, the leaked urine is absorbed into the absorbent core of the leakage absorption portion.

More preferably, the absorbent core comprises a liquid-absorbing layer having a web of liquid-absorbing fibers, and a stop layer is provided between the liquid-absorbing layer and the inner sheet at least in the vicinity of the edge of the opening, the stop layer being formed by a web of fibers which has lower density than that of the liquid-absorbing layer, to function as a cushion.

Because the stop layer wraps the penis following the configuration of the penis, a gap between the penis and the opening is closed, so that urine flowing to the outside is stopped at the stop layer.

Further preferably, the stop layer forms a plurality of protruding portions protruding in a direction toward the inner sheet from the liquid-absorbing layer. By forming the protruding portions, the stop layer can wrap the penis more closely.

When the penis is inserted into the opening, total pressing force exerted by the pair of the elastic members to the penis is preferably 30 to 70 gf.

DETAILED DESCRIPTION OF THE PREFERRED EMBODIMENTS

Figure 1:
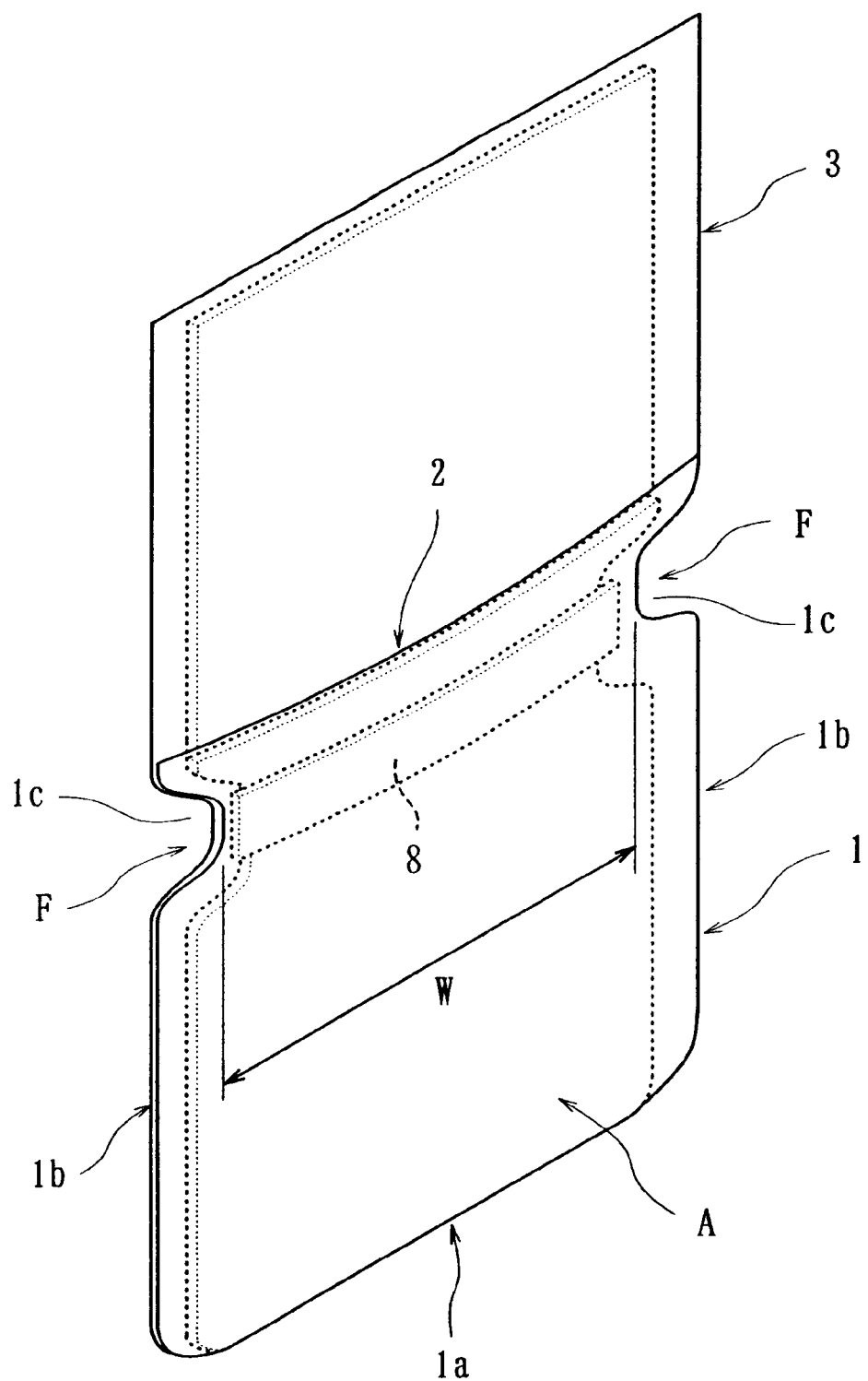
FIG. 1 is a perspective view showing an embodiment of a urine-receiving pad for men of the present invention.
Figure 2:
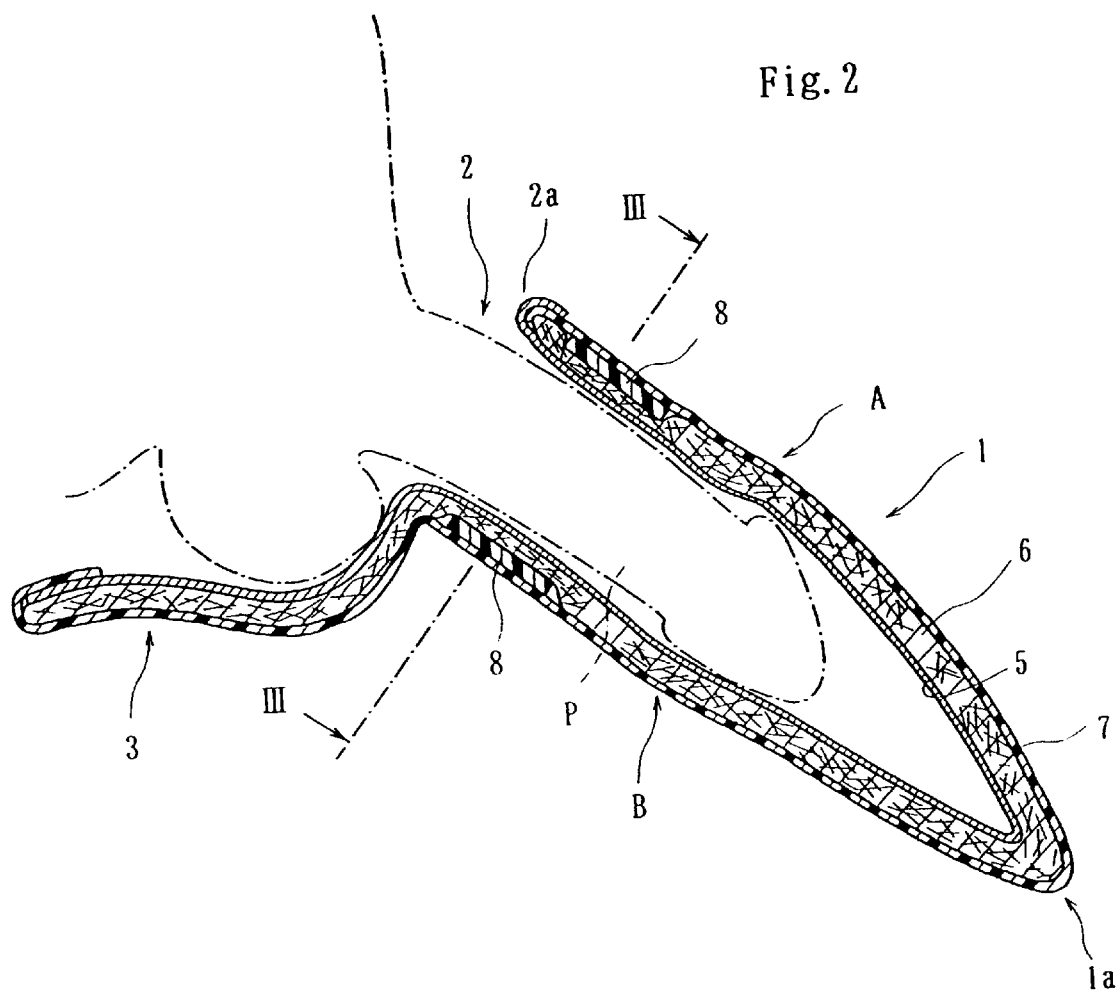
FIG. 2 is a sectional view showing an attached state of the urine-receiving pad for men shown in FIG. 1.
Figure 3:
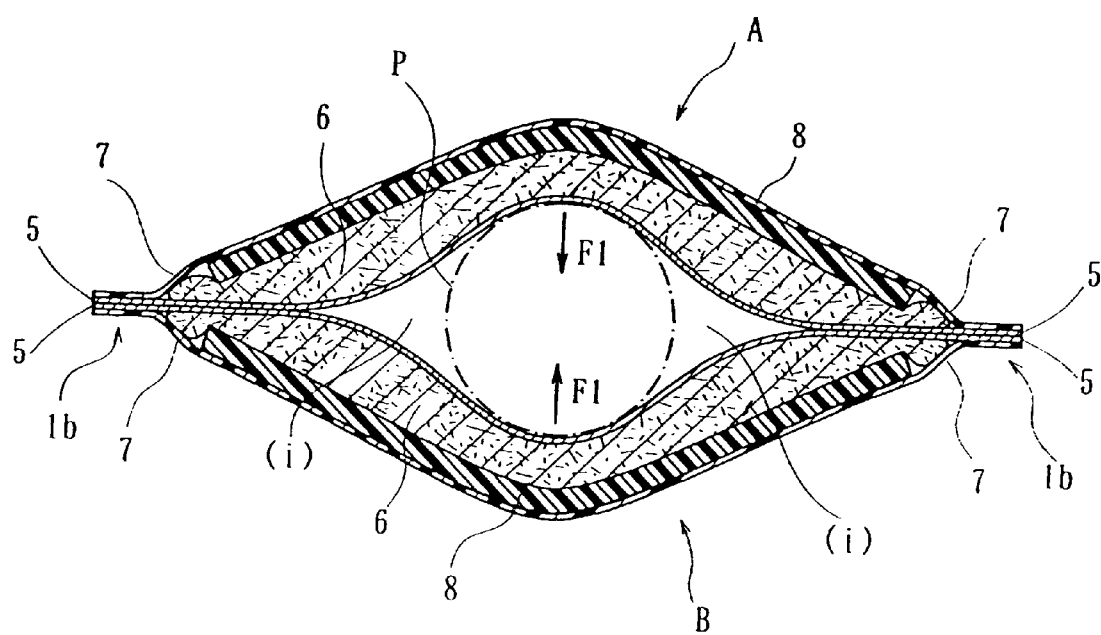
FIG. 3 is a sectional view showing the vicinity of the opening, taken along line III—III of FIG. 2.

FIG. 1 is a perspective view showing the urine-receiving pad for men of the present invention; FIG. 2 is a sectional view showing the attached state of the urine-receiving pad for men; and FIG. 3 is a sectional view taken along the III—III line of FIG. 2.

The urine-receiving pad is mainly composed of a bag 1. The bag 1 is formed with an opening 2 and a leakage absorption portion 3 extending from one edge of the opening 2 in a direction opposite to the bag 1.

The bag 1 and the leakage absorption portion 3 are formed from a laminated sheet as shown in FIG. 2. The laminated sheet has a laminated structure of an inner sheet 5, an outer sheet 7, and an absorbent core 6 sandwiched between the inner sheet 5 and the outer sheet 7.

The inner sheet 5 is a liquid-permeable sheet which is soft for skin of a wearer. The inner sheet 5 is a fiber-confounded non-woven fabric (spunlace non-woven fabric), which is formed of synthetic fibers such as rayon fibers, polyester fibers and polyethylene fibers, or formed of a combination of those fibers. The inner sheet 5 may be provided with a large number of holes to facilitate passage of urine. The outer sheet (back sheet) 7 is formed of a liquid-impermeable, air-permeable and water-proof plastic film or the like.

The absorbent core 6 has particles of super-absorptive polymer (SAP) included in a web of liquid-absorbing fibers such as natural pulp fibers, and the web having SAP are sandwiched between or wrapped with tissue paper.

The bag 1 is constituted by folding the laminated sheet consisting of the inner sheet 5, the absorbent core 6 and the outer sheet 7, into two folded portions A and B, and a folded side thereof serves as a bottom 1a of the bag 1. On one edge 2a of the opening 2, as shown in FIG. 2, the inner sheet 5 and the outer sheet 7 are bonded together by means of a hot melt adhesive. On two sides 1b, 1b shown in FIG. 3, the inner sheet 5 and the outer sheet 7 are bonded together by the hot melt adhesive in the absence of the absorbent core 6 therebetween, and the inner sheet 5 of the folded portion A is further bonded with the inner sheet 5 of the other folded portion B as shown in FIG. 3, by the hot melt adhesive. Accordingly, the bag 1 is opened at the opening 2 only, and the other sides 1b, 1b and the folded side (the bottom 1a) thereof are closed, and the absorbent core 6 is present in the bottom 1a continuously from the folded portion A to the folded portion B and is present inside the sides 1b, 1b in such a manner as shown in FIG. 3 to prevent leakage of urine therefrom.

The folded portion B of the laminated sheet further extends from the opening 2 in the direction opposition to the bag 1, to form a leakage absorption portion 3, wherein the inner sheet 5 faces skin of the wearer.

As shown in FIG. 1, dents 1c, 1c are symmetrically formed in both the sides 1b, 1b of the bag 1 near the opening 2, and the bag 1 has a thinner width dimension W therein than in other portions of the bag 1. A pair of plate-shaped elastic members 8, 8 are provided between the dents 1c, 1c to the folded portions A and B, as shown in FIGS. 2 and 3.

The plate-shaped elastic member 8 is a plastic plate or a cardboard plate. It may also be a cardboard plate impregnated with resin to reinforce elastic force thereby. Further, it may be made of foamed resin such as foamed polyurethane or foamed polyethylene. The elastic member made of the foamed resin is soft and exerts suitable compressing force on the penis and thus the foamed resin is a preferable material. The elastic member 8 is fixed by a hot melt adhesive or the like to the inside of the outer sheet 7, i.e., between the outer sheet 7 and the absorbent core 6. Alternatively, the elastic member 8 may be fixed to the outside of the outer sheet 7.

The width dimension W is preferably set 8 to 12 cm or 10 to 12 cm so that both ends of the elastic member 8 in the width thereof are easily held with the thumb and the forefinger or with the thumb and the middle finger of an adult.

A method of wearing the urine-receiving pad is described hereinafter.

Before the urine-receiving pad is applied to the penis, the folded portions A and B of the laminated sheet are attached to each other at the opening 2 as shown in FIG. 1, by elastic restoration forces of the pair of the elastic members 8, 8, which are in a flat state or in a slightly buckling-deformed state at the present time.

In order to open the opening 2, the thumb and forefinger or the thumb and middle finger are put on dents 1c, 1c of the bag 1, and forces F, F are applied to both the ends of the elastic members 8, 8. As a result, each of the elastic members 8, 8 is buckling-deformed or further buckling-deformed in a separating direction from the other at a central portion thereof, whereby the opening 2 is opened to facilitate insertion of the penis. The tip of the penis P is introduced into the opening 2 thus opened and the opening 2 is then moved to the root of the penis P, as shown in FIG. 2. At this time, the leakage absorption portion 3 is applied below the testes and crotch as shown in FIG. 2.

When the opening 2 reaches the root of the penis P, the fingers holding dents 1c, 1c are removed, so that the penis P is pressed by forces F1 and F1 due to the restoration elastic forces of the buckling-deformed elastic members 8, 8, as shown in FIG. 3. As a result, the opening 2 fits about the root of the penis P and the bag 1 is attached to the penis P securely. With the urine-receiving pad being attached in such a secure manner, a diaper for an adult is thereafter worn.

In the urine-receiving pad of the present invention, the opening 2 is easily opened upon application of forces F, F by holding both the ends of the elastic members 8, 8 with fingers, so that the urine-receiving pad can be held and opened at the opening 2 with only one hand. Therefore, whole attaching operation can be easily completed by using only one hand, followed by inserting the penis P into the opening 2 and taking fingers off the dents 1c, 1c. This attaching operation is feasible without requiring the other hand to hold the penis.

After the completion of attachment, the root of the penis P is sandwiched between the elastic members 8, 8 securely with forces F1, F1 thereof, so that the penis P is prevented from coming out of the urine-receiving pad in the diaper, even if the urine-receiving pad is out of position in the diaper due to wearer's move e.g., turning over.

Because this urine-receiving pad makes use of the elastic member 8 to be buckling-deformed, force F1 exerted by the elastic member 8 to press the penis P is so weak that total pressing force of forces F1, F1 of the elastic members 8, 8 is, for example, about 30 to 70 gf. Accordingly, pressure onto the penis P is small enough to prevent unpleasantness to a wearer. Further, the opening 2 can follow the shape of the penis P in both cases of swelling and shrinking, and force F1 of the elastic member 8 hardly changes even when the penis P is swollen, to ensure that the penis P is constantly maintained under the optimum conditions. Further, in the case where the elastic members 8, 8 exert total pressing force of about 30 to 70 gf upon buckling-deformation as shown in FIG. 3, very low forces F, F are required to buckle the elastic members 8, 8, so that the elastic members 8, 8 can be easily buckling-deformed with fingers by one hand.

When urine is excreted, the urine is absorbed via the inner sheet 5 into the absorbent core 6. Because the bag 1 is closed except for the opening 2, and because the laminated sheet is folded in two at the bottom 1a including the absorbent core 6, the urine is securely absorbed into the bag 1, preventing easy leakage therefrom.

Even if a large volume of urine is excreted and part of the urine is leaked from the opening 2, the leaked urine can be absorbed into the absorbent core 6 of the leakage absorption portion 3 placed below the testes and crotch, and therefore it is possible to prevent a large volume of urine from leaking from the bag 1 into the diaper.

Incidentally, the urine-receiving pad can be removed from the penis P with only one hand as well, by holding the dents 1c, 1c of the bag 1 with fingers and buckling-deforming the elastic members 8, 8 so as to enlarge the opening area of the opening 2. When the fingers are took off the pad after removed, the opening 2 is naturally closed due to the elastic restoration forces of the elastic members 8, 8.

Figure 4:
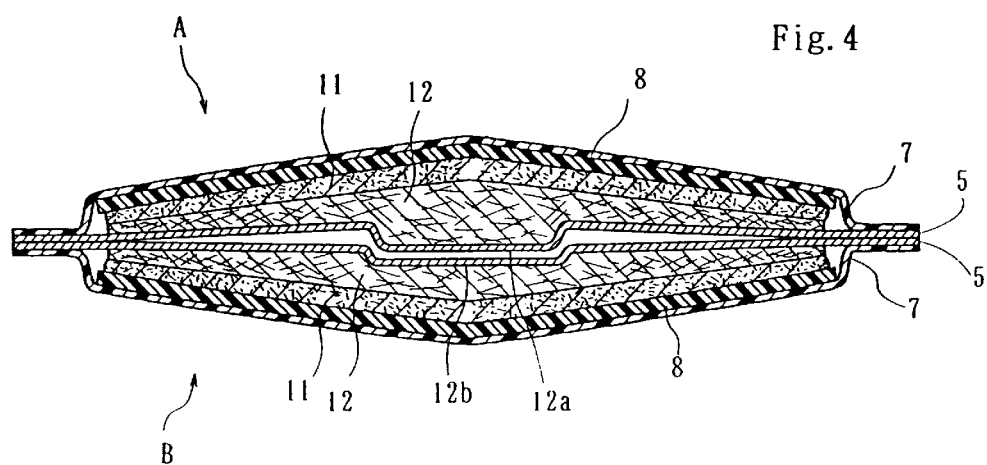
FIG. 4 is a modification to the urine-receiving pad of the present invention, showing a sectional view in the vicinity of the opening without insertion of the penis.
Figure 5:
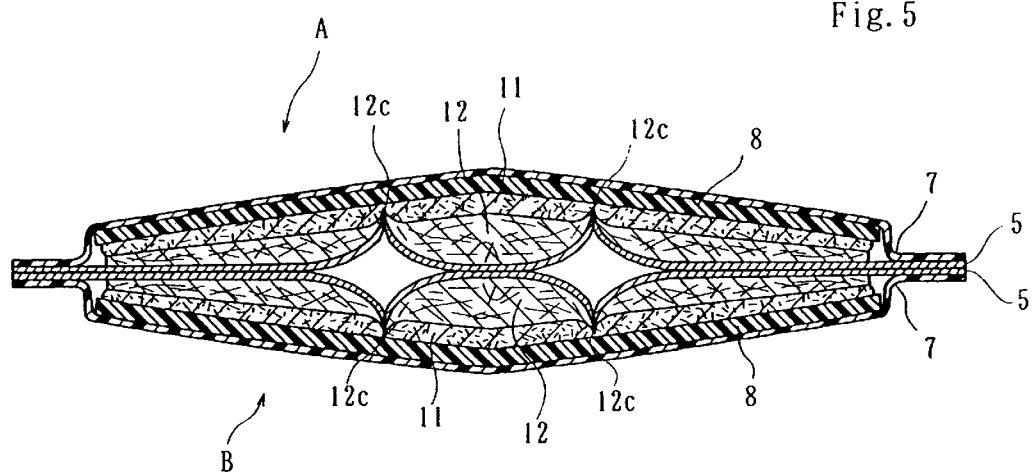
FIG. 5 is another modification to the urine-receiving pad of the present invention, showing a sectional view in the vicinity of the opening without insertion of the penis.

FIGS. 4 and 5 are modifications to the urine-receiving pad of the present invention, each showing a sectional view in the vicinity of the opening 2 (similar to the FIG. 3) without insertion of the penis.

In these modifications, an absorbent core 10, at least in the vicinity of the edge of the opening 2, has a two-layer structure of a liquid-absorbing layer 11 and a stop layer 12 which can function as a cushion, and this stop layer 12 is covered with the inner sheet 5.

The liquid-absorbing layer 11 has particles of super-absorptive polymer (SAP) included in a web of liquid-absorbing fibers such as natural pulp fibers, in the same way as the absorbent core 6 shown in FIG. 3. The stop layer 12 is a web having lower density than that of the web of the layer 11, so as to function as an elastically shrinkable cushion. The web of the layer 12 is formed by fibers having higher elasticity than that of the liquid-absorbing fibers of the layer 11. The fibers of the stop layer 12 mainly include hydrophobic synthetic fibers such as polyester fibers, which may be mixed with water-absorbing fibers such as rayon in case of necessity. The synthetic fibers such as polyester fibers are preferably treated form hydrophilic or sweat-absorbing fibers.

FIG. 4 shows that the stop layer 12 has a convex portion 12a at the center thereof in the width direction in the folded portion A, while having a concave portion 12b corresponding to the convex portion 12a in the folded portion B. In FIG. 5, the stop layer 12 has a so-called quilting shape, wherein the inner sheet 5 covering the stop layer 12 is partially stitched or melt-bonded at portions 12c to form a plurality of convex portions therein.

In FIGS. 4 and 5, when the penis P is pressed by elastic restoration forces of the buckling-deformed elastic members 8, 8, the penis P is enveloped from both sides of the folded portions A and B with the stop layer 12, which serves as a cushion because the stop layer 12 is formed of the low-density web consisting of the highly-elastic fibers, so that gaps (i), (i) between the penis P and the opening 2 shown in FIG. 3 can be closed effectively.

Accordingly, urine tending to leak outside of the bag 1 through the opening 2 is stopped with the stop layer 12, to prevent the leakage of urine through the opening 2.

Incidentally, the elastic member 8 may be provided only to one side of the folded portion A or B. Even then the urine-receiving pad can be attached to the penis in a secure manner.

While this invention has been described as having preferred embodiments, it will be understood that it is capable of further modifications. This application is therefore intended to cover any equivalents, variations, uses, or adaptations of the invention following the general principals thereof, and including such departures from the present disclosure as come within known or customary practice in the art to which this invention pertains and fall within the limits of the appended claims.

What is claimed is:

1. A urine-receiving pad for men comprising:

a bag having an opening, which is formed from at least one laminated sheet having a liquid-permeable inner sheet, a liquid-impermeable outer sheet and an absorbent core provided between both the inner and outer sheets, and the bag for being applied a penis in such a manner that the penis is inserted into the opening; and a pair of plate-shaped or linear elastic members disposed along an edge of said opening for sandwiching the penis by elastic restoration forces of the elastic members in a state of buckling deformation; and wherein the absorbent core comprises a liquid-absorbing layer having a web of liquid-absorbing fibers, and a stop layer is provided between said liquid-absorbing layer and said inner sheet at least in the vicinity of the edge of the opening, said stop layer being formed by a web of fibers which has lower density than a density of said liquid-absorbing layer, to function as a cushion.

2. The urine-receiving pad for men according to claim 1 wherein the laminated sheet is folded in two toward the inner sheet in a laminating direction of the laminated sheet, and a folded side of the laminated sheet forms a bottom of the bag, and the laminated sheet is sealed along sides extending from the folded side, to form the bag having the opening.

3. The urine-receiving pad for men according to claim 1 wherein the laminated sheet is extended from a part of the edge of the opening in a direction opposite to the bottom of the bag to form a leakage absorption portion.

4. The urine-receiving pad for men according to claim 1 wherein the pair of elastic members are made of plastic, paper or cardboard impregnated with reinforcing resin.

5. The urine-receiving pad for men according to claim 1 wherein the pair of elastic members are made of foamed resin.

6. The urine-receiving pad for men according to claim 1 wherein said stop layer forms a plurality of protruding portions protruding in a direction toward the inner sheet from the liquid-absorbing layer.

7. The urine-receiving pad for men according to claim 1 wherein when the penis is inserted into the opening, total pressing force exerted by the pair of the elastic members to the penis is 30 to 70 gf.

\* \* \* \* \*